(12) United States Patent
Van Den Brink

(10) Patent No.: US 8,705,824 B2
(45) Date of Patent: Apr. 22, 2014

(54) APPARATUS AND METHOD FOR ORDERING STORED IMAGES

(75) Inventor: Johan Samuel Van Den Brink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 76 days.

(21) Appl. No.: 13/320,551

(22) PCT Filed: Jun. 3, 2010

(86) PCT No.: PCT/IB2010/052476
§ 371 (c)(1),
(2), (4) Date: Nov. 15, 2011

(87) PCT Pub. No.: WO2010/143103
PCT Pub. Date: Dec. 16, 2010

(65) Prior Publication Data
US 2012/0070048 A1    Mar. 22, 2012

(30) Foreign Application Priority Data

Jun. 9, 2009  (EP) ..................................... 09162249

(51) Int. Cl.
*G06K 9/00*        (2006.01)
(52) U.S. Cl.
USPC ......................................................... 382/128

(58) Field of Classification Search
None
See application file for complete search history.

(56) References Cited

U.S. PATENT DOCUMENTS

| 7,120,644 | B1 | 10/2006 | Canessa et al. |
|---|---|---|---|
| 7,302,164 | B2 | 11/2007 | Wright et al. |
| 7,310,651 | B2 | 12/2007 | Dave et al. |
| 2006/0023928 | A1 | 2/2006 | Assmann |
| 2008/0005059 | A1 | 1/2008 | Colang et al. |
| 2009/0175417 | A1* | 7/2009 | Sasano .......................... 378/98.5 |
| 2009/0279672 | A1* | 11/2009 | Reiner ........................... 378/207 |
| 2009/0290770 | A1* | 11/2009 | Mori et al. ..................... 382/128 |
| 2010/0211409 | A1* | 8/2010 | Kotula et al. ..................... 705/3 |

FOREIGN PATENT DOCUMENTS

| EP | 1903462 A2 | 3/2008 |
|---|---|---|
| EP | 2002782 A2 | 12/2008 |
| WO | 03071779 A1 | 8/2003 |
| WO | 2007026318 A2 | 3/2007 |
| WO | 2009023101 A2 | 2/2009 |

* cited by examiner

*Primary Examiner* — Nirav G Patel

(57) ABSTRACT

An apparatus comprising—an imaging component for acquiring magnetic resonance images;—a storage component for storing the magnetic resonance images in a stack;—a sorting component for sorting the magnetic resonance images in the stack using machine defined meta information of the images; and—an interface for reading the ordered stack.

13 Claims, 3 Drawing Sheets

APPARATUS AND METHOD FOR ORDERING STORED IMAGES

FIELD OF THE INVENTION

The present invention relates to the field of medical imaging, and more precisely to the field of the handling of medical images.

BACKGROUND AND RELATED ART

Medical image acquisitions involve generation of multiple image series, including surveys used to plan the diagnostic scans. When the series are sent to a Picture Archiving and Communication System (PACS), this transfer uses the time order of acquisition of the series. In consequence the non-diagnostic series are the first to show up when opening an examination.

SUMMARY OF THE INVENTION

The present invention provide for an apparatus, a method, and a computer program product in the independent claims. Embodiments of the invention are given in the dependent claims.

Survey and reference scans of medical imaging techniques often have a poor image quality. Because they are acquired as first in time order they are displayed as first when a referring physician opens an examination with a simple image viewer. This is undesired because the survey and reference images are of no relevance for diagnostics. There is a need to move the survey, the reference images and other images with a low image quality or of lower relevance for the medical diagnostics behind the images of a high relevance for the medical diagnostics so that the images with the high relevance are displayed first, when a referring physician opens the files.

In U.S. 2008/0005059A1, a method and system to maintain a personal health record, including, obtaining data using a medical imaging device, storing the data in a picture archiving and communication system, determining which of the data stored in the picture archiving and communication system is to be stored in the personal health record, and transmitting the data to be stored in the personal health record to an internet accessible storage device based on the determination, is disclosed.

In accordance with embodiments of the invention an apparatus is provided for ordering medical images. An imaging component acquires medical images that are stored by a storage component in a stack. The storage component is adapted to store received data on a storage medium. In this stack the images can be in time order of acquisition. A plurality of images that belong together in a clinical logic is called a set of images. Each set of images has machine-defined meta information, for example a header, wherein the type of the set of the images is defined by the system. Meta information is information that describes the images, e.g. the type of scan, the image quality or the relevancy for diagnostics.

A sorting component orders the images in the stack using the machine-defined meta information of the images. Preferably, survey and reference scans used to plan the diagnostic scans are ordered to the end portion of the stack because survey and reference scans are of no importance for a referring physician and often have a poor image quality.

When the sorting component has finished ordering the images in the stack, an interface reads out the ordered stack. The interface is adapted to send the images to a picture archiving and communication system (PACS) or to store them on a DVD or other media.

This is advantageous because when the sets of the images are sent to a picture archiving and communication system (PACS) or file systems on a DVD or other media, the images first in stack are displayed when opening an examination. The survey images with a poor image quality are preferably stored in the end portion of the stack so that they show up after all the other images.

Preferably, the images are stored in Digital Imaging and Computations in Medicine (DICOM) archives viewable with DICOM image viewers.

Another advantage of an embodiment of the invention is that scans are acquired pre and post-contrast which are separated in time order but logically belong together in the reading process. Pre-contrast images are acquired before the person to be examined is given a contrast agent that is used to enhance the contrast of structures or fluids within the body in medical imaging. It is commonly used to enhance the visibility of blood vessels and the gastrointestinal tract. Post-contrast images are acquired after the person to be examined is given the contrast agent. The sorting component can order the images such that clinically logical order is preserved. The meta information can contain information if an image is a pre- or a post-contrast image.

Changing the order of the stored images is advantageous because when the images are sent to PACS in the clinically logical order there is no need for special software for viewing the images from the PACS in the clinically logical order. This is especially advantageous for referring physicians that usually rely on simple image viewers when accessing the images. The ordered sets as created in accordance with embodiments of the invention will first show the most important images and will show the survey scans with the poor image quality last.

In accordance with embodiments of the invention, the apparatus comprises a user interface for entering user meta information that refers to the machine defined meta information of the images. For example, the user defines in the user meta information that a certain scan is most important for the diagnostics. Then, this user defined meta information refers to the machine-defined meta information of the images and defines this certain scan as most important for the diagnostics. This is advantageous because the user can define at least one set of images that is more important than at least one other set of images. For example, a first set of images is more important for the diagnosis than a second set of images. The user can define that the first set is more important than the second set. The sorting component then considers this additional user-defined meta information for sorting the sets of images. The more important sets are sorted to the beginning of the stack so that they are read first after being sent to the PACS. This is advantageous because a referring physician opening the data directly sees the most important set of images instead of survey images that were acquired first.

According to embodiments of the invention a quality determination component determines the quality of the images. For example, this can be done based on the signal to noise ratio or mutual information metrics. A minimum level of the quality is defined by a predefined threshold. When the quality of an image is below this predefined threshold the quality determination component sends a first signal to the sorting component to store the image on the end portion of the stack. Preferably, the quality determination component adds information generated by the quality determination component to the meta information about the image quality. Preferably, the quality determination component sends a second signal to the imaging component to re-acquire the image.

In another embodiment of the invention the second signal is sent to the imaging component by the sorting component after the sorting component has received the first signal from the quality determination component. The re-acquired image is sorted by the sorting component based on the machine-defined meta information of the image to the position in the stack where the image with the image quality below the predefined threshold has been stored before having been moved to the end of the stack.

According to embodiments of the invention a computational unit determines the quality of the images, sorts the images in stack using meta information of the images and sends the second signal to the imaging component to re-acquire the image when the quality of the image is below the predefined threshold.

In accordance with embodiments of the invention the quality determination component is adapted to send a third signal to the user interface when the image quality of the image is below the predefined threshold. The user interface is adapted to send a fourth signal to the imaging component indicating that the image quality is ignored for the further treatment of the image. For example, although the quality of an image is below the threshold, the user may want to use it for the diagnostics.

In accordance with embodiments of the invention the user interface is adapted to send the second signal to the imaging component to re-acquire the image. This is advantageous because the user may desire a re-acquiring of the image, for example because of the need of a high quality standard of the image or other reasons that require a reacquisition of the image, e.g. hospital schedules.

In accordance with embodiments of the invention the sorting component is adapted to separate a plurality of images into a plurality of multiple output sets. During the examination images may belong together that are not acquired one after the other. The sorting component is adapted to sort the images in the clinical logical order. This is advantageous because there is a need to separate dynamic scans (or phases) into multiple output sets, e.g. in magnetic resonance imaging of the liver where four dynamics are acquired, which at PACS are accessed as individual sets with distinctly differing diagnostic information.

In accordance with embodiments of the invention an image processing component processes images of the imaging component and defines the machine-defined meta information of the processed images. This is advantageous because the post processed images can be sorted by the sorting component to the position in the stack where the original image has been stored based on the machine-defined meta information. The original image is sorted to the end portion of the stack by the sorting component because it is less important for the referring physician than the post processed image. Advantageously, a set that results from post-processing steps, e.g. Maximum Intensity Projection (MIP) or more complex cases, where an output set is the result of the combination of a plurality of source sets, and that is of a higher diagnostic value than the source set, is ordered in the beginning portion of the stack by the sorting component based on the machine-defined meta information.

Preferably, the images of one single medical case are stored in one single stack. A medical case usually is one examination of one body part. Preferably, the storage component is adapted to store several medical cases.

Preferably, the medical images handled by the embodiments of the invention are magnetic resonance, positron emission tomography, computed tomography, endoscopy, mammogram, digital radiography, computed radiography images or hybrid modalities.

In another aspect, the invention relates to a method of operating an apparatus according to any of the preceding embodiments of the invention.

In another aspect, the invention relates to a computer program product comprising machine executable instructions for performing the method according to any of the preceding embodiments.

These and other aspects of the invention will be apparent from and elucidated with reference to the embodiments described hereinafter.

BRIEF DESCRIPTION OF THE DRAWINGS

In the following embodiments of the invention are described in greater detail by way of example only making reference to the drawings in which.

DETAILED DESCRIPTION

Figure 1:
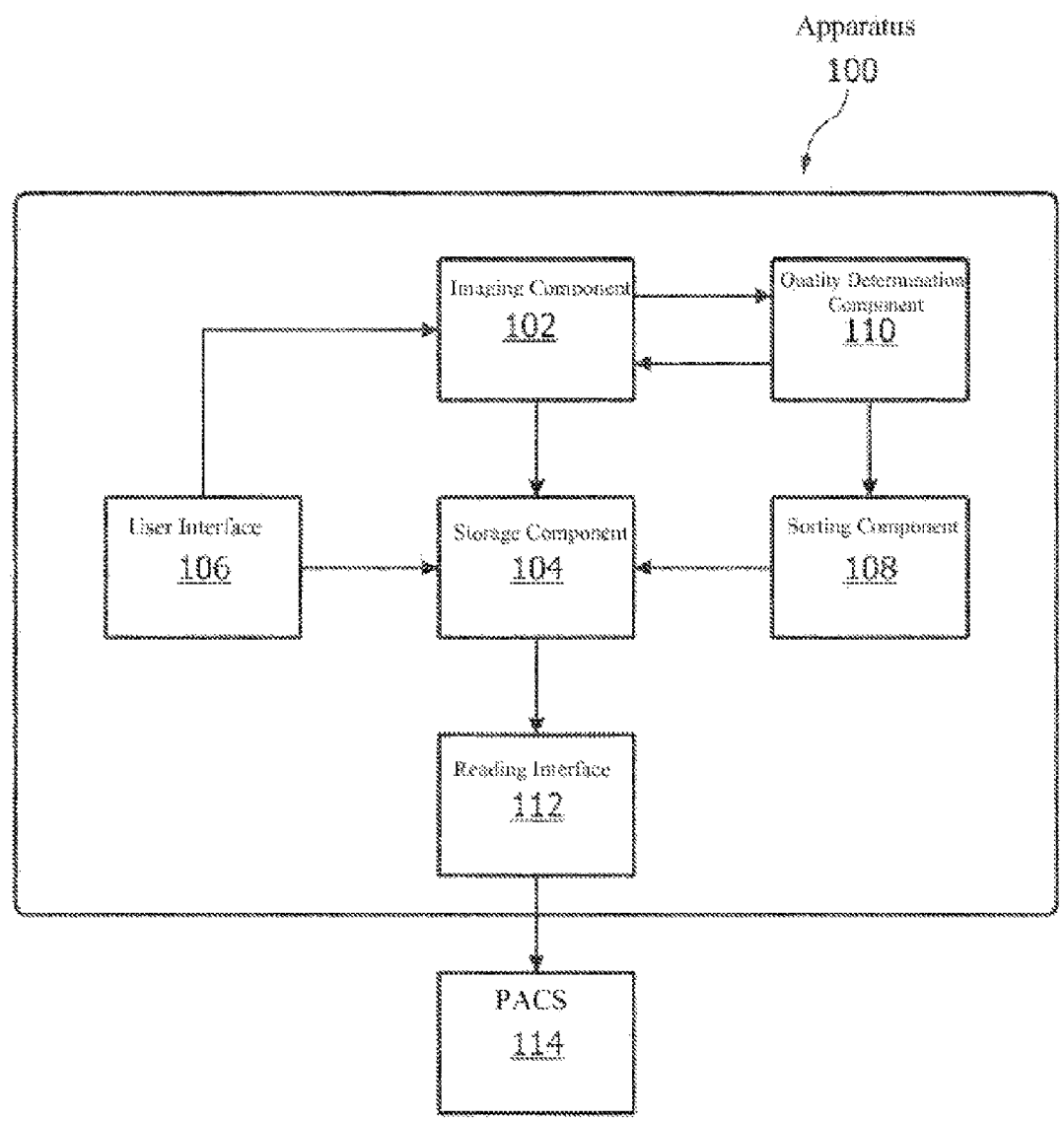
FIG. 1 shows a block diagram of an apparatus according to an embodiment of the invention.

In the following the same reference numerals are used to designate like elements throughout the various embodiments described below.

FIG. 1 shows a block diagram of an apparatus 100 according to an embodiment of the invention. The imaging component 102 acquires images. The images including machine-defined meta information are sent to the storage component 104 and are stored in stack. The user interface 106 is adapted to add user-defined meta information to the stored images in the storage component 104. Further, the user interface 106 is adapted for sending a signal to the imaging component 102 to re-acquire at least one image.

The sorting component 108 defines the order of the images stored in stack in the storage component 104. The ordering is based on the user-defined meta information and on the machine-defined meta information.

Further, the imaging component 102 sends the images to the quality determination component 110. The quality determination component 110 determines the quality of the image. If the quality of the image is below a threshold the quality determination component 110 sends a first signal to the sorting component 108 to order the image in the end of the stack. The quality determination component 110 sends a second signal to the imaging component 102 when the quality is below the threshold to re-acquire the image. Based on the machine-defined meta information the sorting component 108 sorts this newly acquired image to the position of the first acquired image in the stack.

The reading interface 112 is adapted for reading the stack containing the images from the storage component 104 and sending it to a picture archiving and communication system 114, or similar digital archives.

Figure 2:
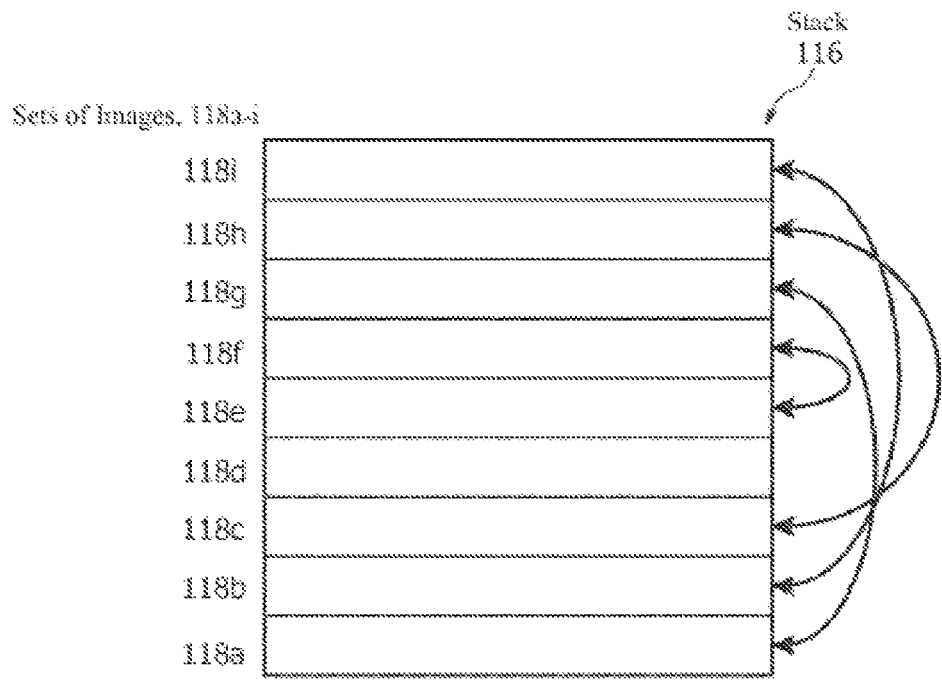
FIGS. 2-5 show schematic views of a stack in a storage component according to an embodiment the invention.

FIG. 2 shows a schematic view of a stack 116 containing several sets of images 118a-118i. The images are stored in time order of acquisition. 118a is the set of images acquired first, 118i is the set of images acquired last. By using the machine-defined meta information and the user-defined meta information the sorting component changes the order of the sets of images in the stack. Preferably, the output order is different from the acquisition order because some images, e.g. reference and survey scans, are less important for the diagnostics than other images. Therefore, the sorting component changes the order of the sets of images.

The sets of images 118a, 118b and 118c are sorted by the sorting component to the end of the stack 116 because of their machine-defined meta information. For example, the sets of images 118a-118c are reference and survey scans. The set of images 118f is stored on the fifth position in the stack 116. For example, this determination is made by the sorting component based on the user-defined meta information.

Figure 3:
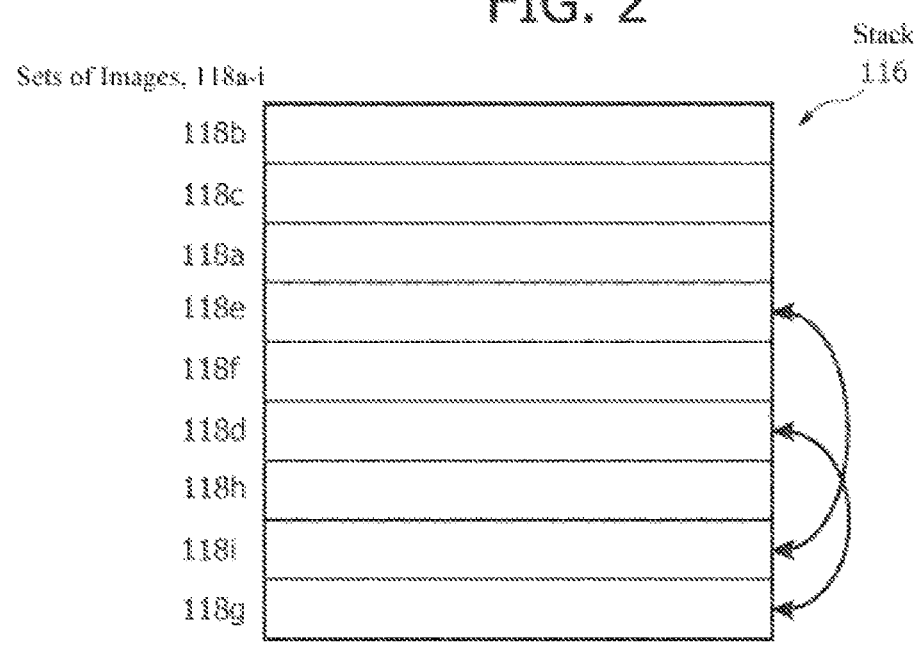

FIG. 3 shows a schematic view of the stack 116 with the changed order of sets of images 118a-118i after being reordered by the sorting component. Based on the user-defined meta information the set of images 118d is ordered in the first portion of the stack 116 because the user has defined the set of images 118d as most important. Further, the user has defined the set of images 118e as the second most important set of images so that the sorting component sorts it to the second position of the stack 116.

Figure 4:
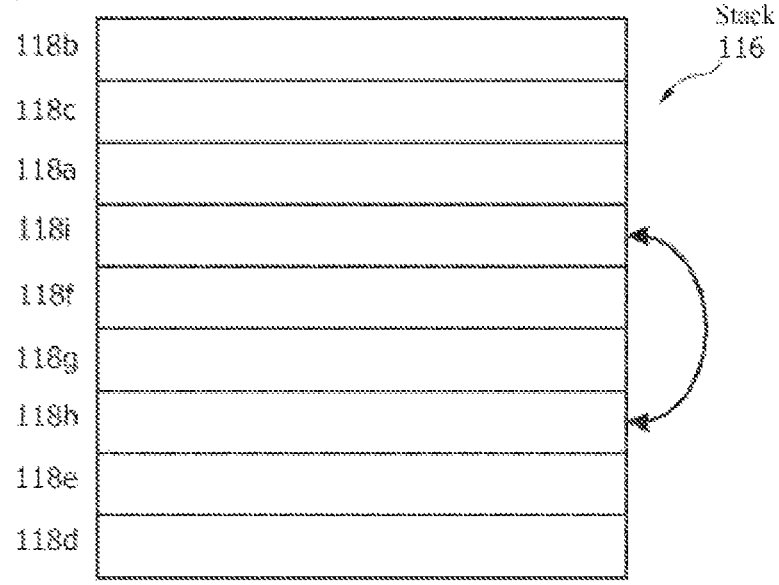

FIG. 4 shows a schematic view of the stack 116 with the changed order of the sets of images 118a-118i. In a last step, e.g. based on the user-defined meta information, the set of images 118i is ordered to the third position in the stack 116 because it is related to the sets of images 118e and 118d.

Figure 5:
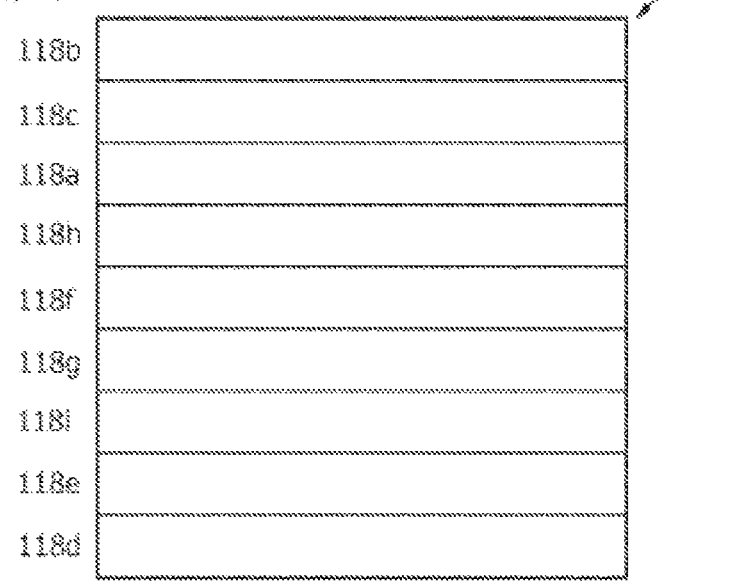

FIG. 5 shows a schematic view of the stack 116 with the final order of the sets of images. The sets of images are sent to the picture archiving and communication system in this order. Hence, a referring physician when opening the stack 116 that refers to one medical case, is provided first with the most important sets of images 118d, 118e and 118i.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be distributed on a suitable medium, such as an optical storage medium or a solid-state medium supplied together with or as part of other hardware, but may also be distributed in other forms. Any reference signs in the claims should not be construed as limiting the scope.

LIST OF REFERENCE NUMERALS

| | |
|---|---|
| 100 | apparatus |
| 102 | imaging component |
| 104 | storage component |
| 106 | user interface |
| 108 | sorting component |
| 110 | quality determination component |
| 112 | reading interface |
| 114 | picture archiving and communication system |
| 116 | stack |
| 118a-i | set of images |

The invention claimed is:

1. An apparatus comprising:
   an imaging component for acquiring medical images;
   a storage component for storing the medical images in a stack, the stack having a beginning portion and an end portion;
   a quality determination component for determining a quality of the images, wherein, when the quality of an image is below a threshold, the quality determination component is adapted for sending a first signal to the sorting component to store the image on the end portion of the stack, and the quality determination component is adapted for sending a second signal to the imaging component to reacquire the image;
   a sorting component for sorting the medical images in the stack using a machine defined meta information of the images and
   an interface for reading the ordered stack.

2. The apparatus of claim 1, comprising a user interface for entering a user meta information referring to the machine defined meta information of the images.

3. The apparatus of claim 2, wherein a computational unit determines the quality of the images, is adapted to modify the meta information of the images, is adapted to sort the images in stack using meta information of the images, and is adapted to send the second signal to the imaging component to reacquire the image when the quality of the image is below the threshold.

4. The apparatus of claim 2, wherein the user interface is adapted to send the second signal to the imaging component to reacquire the image.

5. The apparatus of claim 2, wherein the sorting component sorts at least one image on the end portion based on the machine defined meta information.

6. The apparatus of claim 5, wherein the machine defined meta information is that the image data is not indicated for diagnostic reading, in particular the machine defined meta information being indicative of the image data being a survey scan.

7. The apparatus of claim 1, wherein the sorting component separates a plurality of images into a plurality of multiple output series.

8. The apparatus of claim 1, wherein the sorting component sorts at least one image on the beginning portion of the stack based on the meta information entered by a user referring to the machine defined meta information.

9. The apparatus of claim 1, comprising an image processing component that processes images of the imaging component, and defines the machine defined meta information of the processed images.

10. The apparatus of claim 1, wherein the images of one single medical case are stored in one single stack.

11. The apparatus of claim 10, wherein the storage component is adapted to store several medical cases.

12. A method of operating an apparatus of claim 1, wherein the method comprises:
   acquiring medical images;
   storing the medical images in a stack, the stack having a beginning portion and an end portion;
   determining a quality of the images;
   sorting the medical images in the stack using a machine defined meta information of the images; and
   reading the ordered stack.

13. A computer program product stored on a non-transitory computer readable medium comprising machine executable instructions for performing the method of claim 12.

* * * * *